US007008965B2

(12) United States Patent
Chane-Ching

(10) Patent No.: US 7,008,965 B2
(45) Date of Patent: Mar. 7, 2006

(54) AQUEOUS COLLOIDAL DISPERSION OF A COMPOUND OF CERIUM AND AT LEAST ONE OTHER ELEMENT CHOSEN FROM AMONG THE RARE EARTHS, TRANSITION METALS, ALUMINUM, GALLIUM AND ZIRCONIUM PREPARATION PROCESS AND USE

(75) Inventor: Jean-Yves Chane-Ching, Eaubonne (FR)

(73) Assignee: Rhodia Terres Rares, La Rochelle (FR)

( * ) Notice: Subject to any disclaimer, the term of this patent is extended or adjusted under 35 U.S.C. 154(b) by 173 days.

(21) Appl. No.: 10/182,264

(22) PCT Filed: Jan. 25, 2001

(86) PCT No.: PCT/FR01/00235

§ 371 (c)(1),
(2), (4) Date: Mar. 7, 2003

(87) PCT Pub. No.: WO01/55029

PCT Pub. Date: Aug. 2, 2001

(65) Prior Publication Data

US 2003/0162843 A1 Aug. 28, 2003

(30) Foreign Application Priority Data

Jan. 26, 2000 (FR) .................................. 00 01001

(51) Int. Cl.
*B01F 3/12* (2006.01)
*B01F 17/00* (2006.01)
*C01F 17/00* (2006.01)

(52) U.S. Cl. ....................... 516/78; 516/77; 423/263; 514/937

(58) Field of Classification Search ................. 516/77, 516/78
See application file for complete search history.

(56) References Cited

U.S. PATENT DOCUMENTS

| | | | |
|---|---|---|---|
| 4,231,893 A | | 11/1980 | Woodhead |
| 4,356,106 A | * | 10/1982 | Woodhead et al. ........... 516/89 |
| 4,551,330 A | * | 11/1985 | Wagman et al. .............. 424/59 |
| 4,606,847 A | | 8/1986 | Woodhead |
| 5,776,360 A | * | 7/1998 | Sieber ...................... 252/62.63 |
| 6,358,880 B1 | * | 3/2002 | Hedouin et al. ............. 502/302 |
| 6,475,452 B1 | * | 11/2002 | Hedouin et al. ........... 423/213.2 |

FOREIGN PATENT DOCUMENTS

GB          1 603 794        11/1981

OTHER PUBLICATIONS

Esther M. Conwell, "Conduction (electricity)", in AccessScience@McGraw-Hill, http://www.accessscience.com, DOI 10.1036/1097-8542.155600, last modified: Mar. 14, 2002.*
Frank H. Spedding, "Rare-earth elements", in AccessScience@McGraw-Hill, http://www.accessscience.com, DOI 10.1036/1097-8542.573400, last modified: Apr. 10, 2000.*
Quentin Van Winkle, "Ultrafiltration", in AccessScience@McGraw-Hill, http://www.accessscience.com, DOI 10.1036/1097-8542.719300, last modified: Apr. 10, 2000.*
Egon Matijevic, "Colloid", in AccesScience@McGraw-Hill, http://www.accessscience.com, DOI 10.1036/1097-8542.149100, last modified: Jan. 29, 2001.*
Patent Abstracts fo Japan, vol. 014, No. 090, Feb. 20, 1990 & JP 01 301517 A (Catalyst & Chem. Ind. Co. Ltd.), Dec. 5, 1989.

* cited by examiner

*Primary Examiner*—Randy Gulakowski
*Assistant Examiner*—Timothy J. Kugel
(74) *Attorney, Agent, or Firm*—Buchanan Ingersoll, P.C.

(57) ABSTRACT

The invention relates to an aqueous colloidal dispersion of a compound of cerium and at least one other element M chosen from among the rare earths other than cerium; titanium, vanadium, chromium, manganese, iron, cobalt, nickel, copper, zinc, aluminium, gallium and zirconium.

This dispersion is characterized in that it displays a conductivity of at most 5 mS/cm. It is obtained by a process in which there is reacted with a base a mixture of at least one salt of cerium with at least one salt of an element M mentioned above and in the presence of an acid in a quantity such that the atomic ratio $H^+/(Ce+M)$ is greater than 0.1, then the precipitate from the preceding reaction is re-dispersed in water.

The dispersions of this type cane be used in catalysis, in lubrication, in ceramics, in the manufacture of luminophorous compounds, in cosmetics and as anticorrosion agents.

21 Claims, No Drawings

AQUEOUS COLLOIDAL DISPERSION OF A COMPOUND OF CERIUM AND AT LEAST ONE OTHER ELEMENT CHOSEN FROM AMONG THE RARE EARTHS, TRANSITION METALS, ALUMINUM, GALLIUM AND ZIRCONIUM PREPARATION PROCESS AND USE

The present invention relates to an aqueous colloidal dispersion of a compound of cerium and at least one other element chosen from among the rare earths other than cerium; titanium, vanadium, chromium, manganese, iron, cobalt, nickel, copper, zinc, aluminium, gallium and zirconium.

Cerium sols, quite particularly the sols of tetravalent cerium, are well known. Moreover, cerium sols in combination with another element can be of great benefit, for example for cosmetics applications or in the field of luminophores, and in particular those likely to contain trivalent cerium. However, in these applications, sols are needed which are concentrated and which are pure.

The object of the invention is to resolve such difficulties and thus to obtain concentrated and pure sols, likely in particular to contain trivalent cerium.

The invention thus relates to an aqueous colloidal dispersion of a compound of cerium and at least one other element chosen from among the rare earths other than cerium; titanium, vanadium, chromium, manganese, iron, cobalt, nickel, copper, zinc, aluminium, gallium and zirconium, characterized in that it displays a conductivity of at most 5 mS/cm.

The invention also relates to a process for preparing such a colloidal dispersion which is characterized in there is reacted with a base a mixture of at least one salt of cerium with at least one salt of an element M mentioned above with a base and in the presence of an acid in a quantity such that the atomic ratio $H^+/(Ce+M)$ is greater than 0.1, then the precipitate from the preceding reaction is re-dispersed in water.

Other characteristics, details and advantages of the invention will appear more fully upon reading of the following description, and from the various specific but non-limitative examples intended to illustrate it.

In the remainder of the description, the term colloidal dispersion or sol of a compound of cerium and another element mentioned above means any system constituted of fine solid particles of colloidal dimensions based on oxide and/or hydrated oxide (hydroxide) of cerium and the other element, in suspension in an aqueous liquid phase, the said types also being able, if necessary, to contain residual quantities of bound or adsorbed ions such as for example acetates, citrates, nitrates, chlorides or ammoniums. The percentage of bound ions X or if necessary X+Y, expressed as molar ratio X/ce or (X+Y)/Ce can vary for example between 0.01 and 1.5, more particularly between 0.01 and 1. It will be noted that in such dispersions the cerium and the other element can be found either totally in the form of colloids, or simultaneously in the form of ions or poly-ions and in the form of colloids.

By rare earth is meant the elements of the group constituted by yttrium and the elements of the periodic classification having an atomic number of between 57 and 71 inclusive.

A first characteristic of the dispersion of the invention is its purity. This purity is measured by the conductivity of the dispersion. This conductivity is at most 5 mS/cm. It can be below this value and thus be at most 2 mS/cm and preferably at most 1 mS/cm. More particularly, it can be below 0.3 mS/cm.

According to another characteristic, the dispersion of the invention has a concentration of at least 50 g/l. This concentration is expressed as oxide and taking into account the sum of the oxides of cerium and of the other element or elements mentioned above. This concentration can be more particularly at least 80 g/l.

Another characteristic of the dispersion is that it can contain cerium in oxidation state III. In this case, the level of cerium III is generally at most 50%. It is expressed here and for the whole of the description by the atomic ratio CeIII/total Ce. The level of cerium III can more particularly be at most 35%. Moreover, it is preferably at least 0.5%.

The dispersions of the invention are particularly pure in nitrate anions. More precisely, the nitrate anions content of the dispersions, measured by the nitrate anions content by weight of the colloidal particles, is below 80 ppm. The dispersions of the invention are also pure as regards their chloride ions content.

The quantity of element M is generally at most 50%, this quantity being expressed by the ratio moles of element M/sum of the moles of element M and of cerium. The element M can be present in different states of oxidation. The invention applies of course to dispersions containing several elements M.

The dispersions of the invention can also have a high pH, for example between 5 and 8. These pH values, close to neutral, permit interesting applications of the dispersions of the invention.

The colloidal particles which constitute the sols of the invention are fine. Thus, they can have an average diameter which may be in particular between 2 and 6 nm. This diameter is determined by photometric calculation from a HRTEM (High Resolution Transmission Electron Microscope) analysis.

The process for preparing the dispersions of the invention will now be described.

This process comprises a first stage in which there is reacted with a base a mixture of at least one salt of cerium with at least one salt of an element M. The starting point can be in particular a salt of cerium III or a mixture comprising a salt of cerium IV plus a salt of cerium III.

Products of the hydroxide type in particular may be used as base. Alkali or alkaline-earth hydroxides and ammonia may be mentioned. Secondary, tertiary or quaternary amines may also be used. However, amines and ammonia may be preferred insofar as they reduce the risks of pollution by alkali or alkaline-earth cations. Urea may also be mentioned.

There may be used more particularly as salts of cerium III the acetate, the chloride or the nitrate of cerium III as well as mixtures of these sols such as mixed acetates/chlorides. The nitrate of cerium IV can be used for cerium IV, and the chlorides and the nitrates in particular for the other elements. Salts of the same type can be used for the other element or elements M.

According to a specific characteristic of the process of the invention, the reaction of the salt of cerium with the base takes place in the presence of an acid.

There may be mentioned, as acids likely to be used, the mineral acids and more particularly those corresponding to the salts of cerium, in particular of cerium III, used in the reaction. There may also be mentioned in particular acetic acid, nitric acid or hydrochloric acid.

It should be noted that the acid can also be contributed by the solution of a salt in which it is incorporated. For example, there may be used as starting solution a solution of acid titanium chloride such as $TiOCl_2.2HCl$.

The quantity of acid present or used during the reaction is such that the atomic ratio $H^+/(Ce+M)$ is greater than 0.1, preferably 0.25.

The reaction of the base with the salts can take place continuously, by which is meant a simultaneous addition of the reagents to the reaction medium.

The pH of the reaction medium is usually between 7.6 and 9.5. It is possible to operate in conditions such that the pH of the reaction medium is kept constant during the reaction.

A precipitate is obtained at the end of the aforementioned reaction. This precipitate can be separated from the liquid medium by any known process such as for example by centrifugation. The precipitate thus obtained can then be re-suspended in water so as to give the dispersion of the invention. The concentration of cerium in the dispersion thus obtained is generally between 0.005M and 2M, preferably between 0.05M and 0.25 M.

The precipitate resulting from the reaction can advantageously be washed. This washing can be carried out by placing the precipitate in water then, after stirring, separating the solid from the liquid medium by centrifugation for example. This operation can be repeated several times if necessary.

According to a variant of the invention, the dispersion obtained after re-suspension in water can be purified and/or concentrated by ultrafiltration.

The washing and the ultrafiltration can be carried out under air or in an atmosphere of air and nitrogen or also under nitrogen. The atmosphere under which these operations take place plays a part in the transformation of the cerium III into cerium IV.

After the re-suspension in water and after the optional washing stage and, preferably, before the concentration stage if a concentration is employed, it may be advantageous to carry out an oxidation of the dispersion; the stability of the dispersion is thus improved. This oxidizing treatment can take place in two ways for example.

A first way is to keep the dispersion stirred and under air, for a period which can vary from 3 to 20 hours for example. The second way is to add oxygenated water to the dispersion. The quantity of oxygenated water added is adjusted so as to obtain the CeIII/total Ce ratio, mentioned above, in the final dispersion. This oxidation with the addition of oxygenated water is preferably carried out after a stirring of the dispersion under air for a period of more than 2 hours. The period during which oxygenated air is added can be between 30 min. and 6 hours.

The dispersions of the invention can be used in numerous applications. Catalysis may be mentioned, in particular for automobile post-combustion; in this case the dispersions are used in catalyst preparation. The dispersions can also be employed for lubrication, in ceramics, the production of luminophorous compounds, in cosmetics, and in this case they may be involved in the preparation of cosmetic compositions, in particular in the preparation of anti-UV creams. They can be used on a substrate as anticorrosion agents.

Examples will now be given. In these examples, conductivity is measured with the help of a METROHM 660 CONDUCTOMETER conductivity-measuring apparatus equipped with a TACUSSEL XE100 conductivity cell. The Ce III contents are given as indicated above (atomic ratio CeIII/total Ce).

EXAMPLE 1

This example relates to an aqueous colloidal dispersion of nanometric particles of cerium and titanium with a pH close to neutral. The following are added, accompanied by stirring: 562.8 g of $Ce(CH_3COO)_3$ at 49.3% $CeO_2$ (i.e. 1.6 moles of Ce) and 125 g of $TiOCl_2.2HCl$ at 3.19 mole/Kg of density 1.56 (i.e. 0.4 moles of $TiO_2$). This is made up to 3000 ml with demineralized water. The molar ratio $H^+/(Ce+Ti)$ is 0.4.

The precipitation of the solid is realized in a continuous assembly comprising:
 a one-liter reactor equipped with a fat-paddle stirrer, set at 400 rpm with a tank foot of 0.5 l and a control electrode;
 two feed flasks containing, on the one hand, the solution of salts of cerium described above and, on the other hand, a 3 N ammonia solution.

The flow rate of the solution of cerium acetate and $TiOCl_2$ is fixed at ca. 600 ml/h and the flow rate of the ammonia solution is 340 ml/h. Thus, 2880 ml of the mixture of salts of cerium and titanium and 1630 ml of 3 N ammonia have been added in 288 min.

The pH of the reaction medium is 8.5 throughout the reaction.

A Ce+Ti precipitation yield of 47% is measured.

A precipitate is obtained which is separated by centrifugation.

By calcination at 1000° C., the precipitate is measured as containing 15% oxide of cerium and titanium.

The precipitate is dispersed by adding demineralized water in order to obtain a 0.12 M Ce–Ti dispersion. This is stirred for 15 min. Fresh centrifugation is carried out. Two successive operations are thus realized. The cerium III content of the dispersion is ca. 60%. The dispersion is then stirred under air atmosphere, for a night. At the end of this treatment, the cerium III content of the dispersion is 6.5%, and the total cerium content is 17.2 g/l.

100 ml of the 0.1 M Ce+Ti dispersion are diluted to 300 ml with demineralized water. This is concentrated to 100 ml by ultrafiltration using 3 KD membranes. Three ultrafiltrations are thus carried out. In the last ultrafiltration, the mixture is concentrated in order to obtain a concentrated dispersion with a 5.7% concentration of oxide of cerium and titanium. The pH is 5.4 and the conductivity 1.4 mS/cm. The concentration of nitrate in the colloidal dispersion is less than 80 ppm. By means of MET cryometry, nanometric particles ca. 3 to 4 nm in size are observed.

The dispersion obtained is stable for at least 6 months.

EXAMPLE 2

This example relates to an aqueous colloidal dispersion of nanometric particles of cerium and iron of neutral pH.

The following are placed in a beaker, accompanied by stirring: 307 g of solution of cerium (III) nitrate at 3 M/l $Ce^{3+}$, of density 1.715 and $H^+=0.01$ (i.e. 0.537 mole $Ce^{3+}$), then 194.5 g of solution of $Ce(NO_3)_4$ at $Ce^{4+}=1.325$ M/l, $H^+=0.7$ N, of density 1.44 (i.e. 0.179 moles $Ce^{4+}$), then 73.8 g of $Fe(NO_3)_3.9H_2O$ at 98% (i.e. 0.18 mole), previously dissolved in a total volume of 358 ml (solution at pH 1), then 32.2 g of PROLABO concentrated acetic acid (i.e. 0.54 mole of $CH_3COOH$). This is made up to 2000 ml with demineralized water. The whole is stirred until a solution which is clear to the eye is obtained. The mixture obtained then has a concentration of ca. 0.45 M cerium and iron.

The precipitation of the solid is realized in the continuous assembly described in example 1.

Thus, 2000 ml of the solution of salt of cerium and iron and 800 ml of 3 N ammonia have been added in 240 min.

The colloidal dispersion obtained after re-dispersion under air of the precipitate is washed by ultrafiltration with demineralized water previously adjusted to pH 7.5 then concentrated by ultrafiltration until a concentrated dispersion with a 10.5% concentration of oxide of cerium and iron is obtained.

A colloidal dispersion is thus obtained which is stable for at least 6 months vis-à-vis settling.

EXAMPLE 3

This example relates to an aqueous colloidal dispersion of nanometric particles of cerium and lanthanum with a pH close to neutral.

The following is placed in a beaker, accompanied by stirring: 512 g of cerium acetate at 49.3% $CeO_2$, 208 $cm^3$ concentrated acetic acid, and made up to 3000 ml with demineralized water.

The following are added to 2500 ml of this solution of Ce(III) acetate containing 1.225 mole of Ce: 500 $cm^3$ of a solution of acetate of La(III) at 0.57 M La, i.e. 0.285 mole of La. The molar ratio $H^+/(Ce+La)$ is 2.0.

The precipitation of the solid is realized in the continuous assembly described in example 1.

Thus, 2670 ml of the solution of acetate of cerium-lanthanum and 1971 ml of 3 N ammonia have been added in 287 min.

The pH of the reaction medium is 8.5 throughout the reaction.

A Ce+La precipitation yield of 85% is measured.

A precipitate is obtained which is separated by centrifugation.

By calcination at 1000° C., the precipitate is evaluated at 21% oxide of cerium and lanthanum.

The precipitate is dispersed by adding demineralized water in order to obtain a 0.15 M Ce+La dispersion. This is stirred for 15 min. Fresh centrifugation is carried out. Two successive operations are thus realized. The cerium III content of the dispersion is 80%. The dispersion is then stirred under air atmosphere, for a night. At the end of this treatment, the cerium III content of the dispersion is 5%.

100 ml of the 0.15 M Ce+La dispersion are diluted to 300 ml with demineralized water. This is concentrated to 100 ml by ultrafiltration using 3 KD membranes. Three ultrafiltrations are thus carried out. In the last ultrafiltration, the mixture is concentrated in order to obtain a concentrated dispersion with a 15.5% concentration of oxide of cerium and lanthanum. The pH is 5.5 and the conductivity 0.24 mS/cm. The concentration of nitrate ions in the colloidal dispersion is less than 80 ppm. By means of MET cryometry, nanometric particles ca. 3 to 4 nm in size are observed.

A colloidal dispersion is thus obtained which is stable for at least 6 months vis-à-vis settling.

EXAMPLE 4

This example relates to an aqueous colloidal dispersion of nanometric particles of cerium and aluminium with a pH close to neutral.

The following are placed in a beaker, accompanied by stirring: 585 g of cerium acetate at 49.3% $CeO_2$ (1.67 moles of Ce), 101 g of $AlCl_2, 9H_2O$ ($M_w$=241 g/mole, 0.42 mole of Al) and 103 g of 10 M HCl, and made up to 3000 ml with demineralized water. The molar ratio $H^+/(Ce+Al)$ is 0.5.

The precipitation of the solid is realized in the continuous assembly described in example 1.

Thus, 2440 ml of this solution of acetate of cerium-aluminium and 1580 ml of 3 N ammonia have been added in 244 min.

The pH of the reaction medium is 8.5 throughout the reaction.

A precipitation yield of 64% is measured.

A precipitate is obtained which is separated by centrifugation.

By calcination at 1000° C., the precipitate is evaluated at 8.1% oxide of cerium and aluminium.

The precipitate is dispersed by adding demineralized water in order to obtain a 0.25 M Ce+Al dispersion. This is stirred for 15 min. Fresh centrifugation is carried out. Two successive operations are thus realized. The cerium III content of the dispersion is 60%. The dispersion is then stirred under air atmosphere, for a night. At the end of this treatment, the cerium III content of the dispersion is 31%.

100 ml of the 0.25 M Ce+Al dispersion are diluted to 300 ml with demineralized water. This is concentrated to 100 ml by ultrafiltration using 3 KD membranes. Three ultrafiltrations are thus carried out. In the last ultrafiltration, the mixture is concentrated in order to obtain a concentrated dispersion with a 10.6% concentration of oxide. The pH of the dispersion is 6.

A colloidal dispersion is thus obtained which is stable for at least 6 months vis-à-vis settling.

What is claimed is:

1. An aqueous colloidal dispersion of a compound of cerium and at least one other element M selected from the group consisting of rare earths other than cerium and titanium, vanadium, chromium, manganese, iron, cobalt, nickel, copper, zinc, aluminium, gallium and zirconium, which displays a conductivity of at most 5 mS/cm, and which has a pH of between 5 and 8.

2. The dispersion according to claim 1, wherein the conductivity is at most 2 mS/cm.

3. The dispersion according to claim 2, wherein the conductivity is at most 1 mS/cm.

4. The dispersion according to claim 3, wherein the conductivity is below 0.3 mS/cm.

5. The dispersion according to claim 1, wherein the cerium is a cerium (IV) compound and the dispersion further contains cerium III.

6. The dispersion according to claim 5, which has a level of cerium III relative to the total cerium of at most 50%.

7. The dispersion according to claim 1, which has a concentration of cerium oxide and of at least one other element mentioned above at least 50 g/l.

8. The dispersion according to claim 1, which contains a quantity of element M of at most 50%, expressed by the ratio moles of element M/sum of the moles of element M and of cerium.

9. The dispersion according to claim 1, wherein the colloidal particles have a nitrate content of less than 80 ppm.

10. An anticorrosion agent, comprising the dispersion according to claim 1.

11. A catalyst, comprising the dispersion as claimed in claim 1.

12. A cosmetic composition, comprising the dispersion as claimed in claim 1.

13. The dispersion according to claim 1, wherein the compound is an oxide or hydrated oxide.

14. A process for preparing a colloidal dispersion of a compound of cerium and at least one other element M selected from the group consisting of rare earths other than cerium and titanium, vanadium, chromium, manganese, iron, cobalt, nickel, copper, zinc, aluminium, gallium and zirconium, which displays a conductivity of at most 5 mS/cm, the process comprising reacting a base mixture of at least one salt of cerium with at least one salt of an element M in the presence of an acid in a quantity such that the atomic ratio $H^+/(Ce+M)$ is greater than 0.1; then the precipitate from the preceding reaction is re-dispersed in water.

15. The process according to claim 14, wherein, after the re-dispersion in water of the precipitate, the dispersion obtained is purified by ultrafiltration.

16. The process according to claim 15, wherein, after the re-dispersion in water of the precipitate, the dispersion is subjected to an oxidative treatment.

17. The process according to claim 16, wherein the oxidizing treatment is effected either by stirring under air of the dispersion, or by addition of oxygenated water.

18. The process according to claim 14, wherein the salt of cerium is a salt of cerium III.

19. The process according to claim 14, wherein the reaction is effected continuously.

20. The process according to claim 2, wherein the dispersion has a pH of between 5 and 8.

21. The process according to claim 2, wherein the compound is an oxide or hydrated oxide.

* * * * *